(12) United States Patent
Hashimshony (10) Patent No.: US 7,184,824 B2
(45) Date of Patent: *Feb. 27, 2007

(54) METHOD AND SYSTEM FOR EXAMINING TISSUE ACCORDING TO THE DIELECTRIC PROPERTIES THEREOF

(75) Inventor: Dan Hashimshony, Givat Ada (IL)

(73) Assignee: Dune Medical Devices Ltd., Caesaria (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/965,752

(22) Filed: Oct. 18, 2004

(65) Prior Publication Data

US 2005/0107718 A1    May 19, 2005

Related U.S. Application Data

(63) Continuation of application No. 10/035,428, filed on Jan. 4, 2002, now Pat. No. 6,813,515.

(51) Int. Cl.
    *A61B 5/05* (2006.01)
(52) U.S. Cl. ..................................... 600/547
(58) Field of Classification Search ................ 600/306, 600/547, 554; 606/32–34, 41; 324/642–646, 324/632
    See application file for complete search history.

(56) References Cited

U.S. PATENT DOCUMENTS

| | | | |
|---|---|---|---|
| 4,291,708 A | 9/1981 | Frei et al. | |
| 4,344,440 A | 8/1982 | Aaby et al. | |
| 4,458,694 A | 7/1984 | Sollish et al. | |
| 4,537,203 A | 8/1985 | Machida | |
| 4,539,640 A | 9/1985 | Fry et al. | |

(Continued)

FOREIGN PATENT DOCUMENTS

DE         3637549       5/1988
WO  PCT WO 01/65240    7/2001

OTHER PUBLICATIONS

Misra et al. "Noninvasive Electrical Characterization of Materials at Microwave Frequencies Using An Open-Ended Coaxial Line: Test of An Improved Calibration Technique", IEEE Trans. On Microwave Theory & Techniques, 38(1): 8-13, 1990.

(Continued)

*Primary Examiner*—Max F. Hindenburg
*Assistant Examiner*—Brian Szmal (57) ABSTRACT

A probe, method and system for examining tissue in order to differentiate it from other tissue according to the dielectric properties of the examined tissue are provided. The probe includes an inner conductor, having a plurality of sharp, thin, conductive spikes, at a proximal end with respect to a tissue for examination, the plurality of sharp, thin, conductive spikes being operative to enhance the electrical fringe fields, where interaction with the tissue for examination occurs. The method includes: applying the probe to the tissue to be examined, such that the probe generates an electrical fringe field in the zone of the examined tissue and produces a reflected pulse therefrom with negligible radiation penetrating into the tissue itself; detecting the reflected electrical pulse; and comparing electrical characteristics of the reflected electrical pulse with respect to the applied electrical pulse to provide an indication of the dielectric properties of the examined tissue.

5 Claims, 7 Drawing Sheets

U.S. PATENT DOCUMENTS

| | | | |
|---|---|---|---|
| 4,617,939 A | | 10/1986 | Brown et al. |
| 5,143,079 A | | 9/1992 | Frei et al. |
| 5,227,730 A | * | 7/1993 | King et al. .................. 324/632 |
| 5,704,355 A | | 1/1998 | Bridges |
| 5,744,971 A | * | 4/1998 | Chan et al. .................. 324/643 |
| 5,807,257 A | | 9/1998 | Bridges |
| 5,821,410 A | * | 10/1998 | Xiang et al. ................... 73/105 |
| 5,829,437 A | | 11/1998 | Bridges et al. |
| 5,900,618 A | * | 5/1999 | Anlage et al. ........... 250/201.3 |
| 6,026,323 A | * | 2/2000 | Skladnev et al. ........... 600/547 |
| 6,061,589 A | | 5/2000 | Bridges et al. |
| 6,109,270 A | | 8/2000 | Mah et al. |
| 6,173,604 B1 | | 1/2001 | Xiang et al. |
| 6,233,479 B1 | | 5/2001 | Haddad et al. |
| 6,287,302 B1 | * | 9/2001 | Berube ........................ 606/33 |
| 6,370,426 B1 | * | 4/2002 | Campbell et al. ........... 600/547 |
| 6,597,185 B1 | * | 7/2003 | Talanov et al. ............. 324/638 |
| 6,813,515 B2 | * | 11/2004 | Hashimshony .............. 600/547 |
| 2003/0187366 A1 | | 10/2003 | Hashimshony |

OTHER PUBLICATIONS

Burdette et al. "In Vivo Probe Measurement Technique for Determining Dielectric Properties at VFW Through Microwave Frequencies", IEEE Trans. on Microwave Theory & Techniques, MTT-28(4): 414-427, 1980.

Xu et al. "Measurement of Microwave Permittivity Using Open Ended Elliptical Coaxial Probes", IEEE Trans. on Microwave Theory & Techniques, 40(1): 143-150, 1992.

Stuchly et al. "Measurement of Radio Frequency Permittivity of Biological Tissues With An Open-Ended Coaxial Line: Part II—Experimental Results", IEEE Trans. on Microwave Theory & Techniques, MTT-30(1): 87-91, 1982.

Mosig et al. "Reflection of An Open-Ended Coaxial Line", IEEE Trans. on Instr. & Measur., IM-30(1): 46-51, 1981.

* cited by examiner

METHOD AND SYSTEM FOR EXAMINING TISSUE ACCORDING TO THE DIELECTRIC PROPERTIES THEREOF

CROSS REFERENCE TO RELATED APPLICATION

This application is a continuation of U.S. patent application Ser. No. 10/035,428, filed on Jan. 4, 2002, now U.S. Pat. No. 6,813,515, issued on Nov. 2, 2004.

FIELD AND BACKGROUND OF THE INVENTION

The present invention relates to a method and apparatus for examining tissue in order to differentiate the examined tissue from other tissue according to the dielectric properties of the examined tissue. The invention is particularly useful to differentiate cancerous tissue, particularly breast cancer tissue, from normal, healthy tissue.

Breast cancer is the second leading cause of cancer deaths in women today (after lung cancer) and is the second most common form of cancer among women (after skin cancer). According to the World Health Organization, more than 1.2 million people will be diagnosed with breast cancer this year worldwide. The American Cancer Society estimates that in 2001, approximately 192,200 new cases of invasive breast cancer (Stages I–IV) will be diagnosed among women in the United States; and another 46,400 women will be diagnosed with ductal carcinoma in situ (DCIS), a non-invasive breast cancer. Though much less common, breast cancer also occurs in men, it being estimated that 1,500 cases will be diagnosed in men in 2001. It is further estimated that 40,600 deaths will occur in 2001 from breast cancer (40,200 among women, 400 among men) in the United States. The incidence rate of breast cancer (number of new breast cancers per 100,000 women) increased by approximately 4% during the 1980s but leveled off, to 100.6 cases per 100,000 women, in the 1990s. The death rates from breast cancer also declined significantly between 1992 and 1996, with the largest decreases being among younger women. Medical experts attribute the decline in breast cancer deaths to earlier detection and more effective treatments.

Mammography is currently the best available screening modality for early detection of breast cancer. If the mammography finds a subspecies legion, the individual is directed to undergo a biopsy or other advanced screening methods, like ultrasound or MRI CT etc. Only 20% of the women that undergo a biopsy proceed to a surgical treatment. The traditional method for histological confirmation involves open surgery biopsy. An alternative is image guided biopsy, which is less invasive and more costly. The total number of breast biopsies in the U.S. is about 1.2 M per year. The open biopsy itself is a surgical procedure in which the breast is open and the tumor or lump is taken out, preferably fully.

The traditional method of biopsy, however, is not always successful and fails to successfully remove the appropriate lesion in about 0.5–17% of the cases. Some of the reasons given for unsuccessful biopsies include: 1) poor radiological placement of the localization wire; 2) preoperative and intraoperative dislodgment of the wire; 3) surgical inaccuracy and inadequacy in excising the appropriate tissue; 4) failure to obtain a specimen radiograph; and 5) failure by the pathologist to locate the focus of the disease when searching through a larger tissue sample provided by the surgeon.

All of the above reasons stem from a fundamental problem that during the surgery, the surgeon does not have a real time indication or delineation of the tumor. Because of the difficulty in precisely delineating the cancerous tissue, the surgeon may cut out more than was really necessary to better assure that the entire tumor was removed.

Today, women with stage I and stage II breast cancer are candidates for treatment with modified radical mastectomy and with immediate reconstruction. Breast-conserving therapy (BCT) is also available. Breast conservation therapy consists of surgical removal of a breast nodule and of the auxiliary fat pad containing the auxiliary lymph nodes (about a quarter of the breast). This is followed by radiation therapy to the breast and auxiliary areas in some cases. In this type of operation, precise margin assessment or delineation of the cancerous tissue during the operation is crucial to the success of the procedure since the goal is to remove the tumor completely while minimizing damage to the breast.

This trade-off between complete removal of the tumor, and conservation of the breast, is usually difficult to optimize because the surgeon generally does not know the actual margins of the tumor. If the surgeon were able to clearly delineate the tumor margins during the operation by an on-line margin detector, this trade-off could be better optimized.

The ability of recognizing cancer cells, and especially breast cancer cells, using bioimpedance is well established in the biomedical literature[5,6,7,8]. The usual method for measuring bioimpedance is by introducing a sample into a special chamber and applying an AC current through it while recording the voltage across the sample at each frequency[9,10]. More modern methods rely on multiple electrode matrices which are connected with the human body and measure physiological and pathological changes. Some of the methods aim to localize tumor cells inside the human body and to form an image[11,12]. Although this method is approved by the FDA, it lacks the necessary accuracy for a screening device mainly because of the inherent limitations of long wavelengths and noise from the contact electrodes.

Another technique, based on magnetic[13] bioimpedance, measures the bioimpedance by magnetic induction. This technique consists of a single coil acting as both an electromagnetic source and a receiver operating typically in the frequency range 1–10 MHz. When the coil is placed in a fixed geometric relationship to a conducting body, the alternating electric field in the coil generates electrical eddy current. A change in the bioimpedance induces changes in the eddy current, and as a result, a change in the magnetic field of those eddy currents. The coil acts as a receiver to detect such changes. Experiments with this technique achieved sensitivity of 95%, and specificity of 69%, distinguishing between 1% metastasis tumor and 20% metastasis tumor. Distinguishing between tumor and normal tissue is even better.

Although the exact mechanism responsible for tissue impedance at certain frequencies is not completely understood, the general mechanism[14,15] is well explained by semi-empirical models that are supported by experiments[16,17,18].

Variations in electrical impedance of the human tissue are described in the patent literature to provide indications of tumors, lesions and other abnormalities. For example, U.S. Pat. Nos. 4,291,708; 4,458,694; 4,537,203; 4,617,939 and 4,539,640 exemplify prior art systems for tissue characterization by using multi-element probes which are pressed against the skin of the patient and measure impedance of the tissue to generate a two-dimensional impedance map. Other prior techniques of this type are described in WO 01/43630; U.S. Pat. Nos. 4,291,708 and U.S. 5,143,079. However, the above devices use a set of electrodes that must be electrically contacted with the tissue or body, and therefore the contact is usually a source of noise and also limits maneuverability of the probe over the organ.

Other prior patents, for example U.S. Pat. Nos. 5,807,257; 5,704,355 and 6,061,589 use millimeter and microwave devices to measure bioimpedance and to detect abnormal tissue. These methods direct a free propagating radiation, or a guided radiation via waveguide, onto the organ. The radiation is focused on a relatively small volume inside the organ, and the reflected radiation is then measured. However, these methods lack accuracy and spatial resolution since they are limited by the diffraction limit.

Another prior art technique is based on measurement of the resonance frequency of a resonator as influenced by the tissue impedance. This technique also uses radiation from an antenna, usually a small dipole antenna attached to a coaxial line. Although non-contact, the device actually measures average values inside the organ, and its ability to detect small tumor is doubtful. Similar prior art is described in Xu, Y., et al. "Theoretical and Experimental Study of Measurement of Microwave Permitivity using Open Ended Elliptical Coaxial Probes". IEEE Trans AP-40(1), January 1992, pp 143–150.3. U.S. Pat. No. 6,109,270 (2000 NASA) describes a measurement concept with a multi-modality instrument for tissue identification in real-time neuro-surgical applications.

Other known prior art includes an open-ended coaxial[2,3,4] probe having a center conducting wire surrounding by an insulator and enclosed in an external shield. This type of tip generates both a near field evanescent wave and a far field propagating wave. The propagating wave is undesirable because it interferes with the near field evanescent wave. In order to minimizes the propagating wave, researchers attempted to use coaxial cable with smaller and smaller diameters. But eventually large energy losses and difficult construction limited this direction.

Other existing medical instruments provide general diagnoses for the detection of interfaces between different types of tissues, such as cancerous tissue and healthy tissue, etc. However, such detections have been limited clinically to pre-operative scans, or demand large scanning multi-million-dollar machines, like the MRI, CT, and Mammography. Furthermore, real-time attempts to use these detecting methods are very sensitive to movement of the body, and cannot really be used to position the cutting knife or the biopsy needle. Existing devices provide diagnostic data of limited use since the tissues sampled or removed, depends entirely upon the accuracy with which the localization provided by the preoperative CT, MRI, or US scan is translated to the intracranial biopsy site. Any movement of the organ or the localization device results in an error in biopsy localization. Also, no information about the tissue being cut by the needle or knife is provided.

Detecting breast cancer tissues by measuring bioimpedance is thus well established, and the ability of this technique for delineating cancerous cells inside the body has been proved. However, there is currently no reliable real-time bioimpedance measuring device of sufficiently high accuracy for local tissue characterization and of a spatial resolution comparable to that provided by mammography.

SUMMARY OF THE INVENTION

An object of the present invention is to provide a probe, a method, and also a system, having advantages in one or more of the above respects for examining tissue in order to differentiate the examined tissue from other tissue according to the dielectric properties of the examined tissue. Another object of the invention is to provide a method and system enabling more precise differentiation in a real-time manner of cancerous tissue from healthy, normal tissue.

According to one broad aspect of the present invention, there is provided a probe for examining tissue in order to differentiate it from other tissue according to the dielectric properties of the examined tissue, the probe comprising:

an inner conductor, which defines a general diameter section and a proximal end with respect to a tissue for examination;

an insulation layer, which substantially surrounds the inner conductor; and an outer conductor, which substantially surrounds the inner conductor and the insulator layer, the probe being configured for applying an electric pulse to the tissue for examination, generating electrical fringe fields in the tissue, in a near field, responsive to the electric pulse, applied thereto, thus producing a reflected electric pulse from the tissue for examination, wherein the inner conductor includes at least one section of a different cross-section from that of the general diameter section, the different cross section leading to sharp edges, wherein concentrated electrical charges at the sharp edges enhance the electrical fringe fields at the proximal end, where interaction with the tissue for examination occurs, and wherein the at least one section of the different cross-section comprises a plurality of sharp, thin, conductive spikes, which enhance the electrical fringe fields at the proximal end, where the interaction with the tissue for examination occurs.

According to a more specific aspect of the present invention, there is provided a method of examining tissue in order to differentiate it from other tissue according to the dielectric properties of the examined tissue, comprising: providing a probe having an inner conductor insulated from, and enclosed by, an outer conductor open at one end and extending slightly past the inner conductor in the axial direction, to define an open cavity at one end of the probe; applying the probe to the tissue to be examined such that the examined tissue closes the open cavity at the one end of the probe; applying, via a transmission line at the opposite end of the probe, an electrical pulse which generates an electrical fringe field in the cavity closed by the examined tissue, and which produces a reflected electrical pulse therefrom; detecting the reflected electrical pulse; and comparing electrical characteristics of the reflected electrical pulse with respect to the applied electrical pulse to provide an indication of the dielectric properties of the examined tissue.

The electrical fringe field is an electrical field that exists at the edges of a charged conductor. Usually an electrical fringe field is a DC field, but in the present case, it is a time-dependent field since its source is a voltage pulse. The open cavity defined by the inner and outer conductors serves as a small capacitor probe in which the electrical fringing field is generated between the inner and outer conductors. When a pulse is transmitted through the transmission line to the probe open cavity of the probe closed by the tissue being examined, the pulse is reflected back to the transmission line. Generally speaking, the reflection depends on the impedance of the region at the open cavity of the probe, which impedance depends on the dielectric properties of the examined tissue closing the open end of the cavity. Accordingly, the reflected pulse carries with it information about the dielectric properties of the examined tissue. These properties produce a change in the time-domain-profile of the reflected pulse.

The electrical characteristics of the reflected electrical pulse are compared with those of the applied (incident) electrical pulse by sampling both electrical pulses at a plurality of spaced time intervals, e.g., every 0.2 nanoseconds, and comparing the voltage magnitudes of the two electrical pulses at the spaced time intervals. Both pulses are then transformed by a FFT function to the frequency domain, i.e., amplitude and phase for each frequency. The reflection coefficient is then calculated in the frequency domain; and the frequency dependent complex impedance of the tissue is then calculated using the theoretical relation between impedance and reflection.

It will thus be seen that when the examined tissue is placed in the region of the open cavity define by the inner and outer conductors of the probe, the electrical fringe field penetrates into the open cavity. This penetration is due to the relatively low conductivity of the tissue. Since the electrical fringe field penetrates the tissue, the build-up profile of the electrical fringe field depends on the dielectrical properties of the tissue which produce the changes in the reflected electrical pulse generated by the application of the applied (incident) electrical pulse to the open cavity.

According to further features in the preferred embodiments of the invention described below, the inner conductor includes a tip within the open cavity, which tip is formed with at least two different diameters for enhancing the electrical fringe field. Preferably, the tip of the inner conductor carries a plurality of sharp, thin, electrically-conductive projections, or spikes, for enhancing the electrical fringe field. In the preferred embodiment described below the thickness of these projections or spikes, when used, is from a few microns to about 200 microns.

Preferably, the above-obtained electrical characteristics of the examined tissue are compared with previously stored dielectric projections of known normal and cancerous tissues to constitute a first level of characterization of the examined tissue. A second level of characterization of the examined tissue may be effected to reduce ambiguities by comparing the Cole-Cole parameters of the examined tissue with those previously stored of known normal and cancerous tissues. A third level of characterization of the examined tissue may be effected to further reduce ambiguities by comparing similarities between three-dimensional curves of the examined tissue with those previously stored of known normal and cancerous tissues.

As will be described more particularly below, the method of the present invention, being based on the generation of an electrical fringe field with negligible radiation penetrating into the tissue itself, eliminates almost completely the propagating wave, while the evanescent wave reflections are reduced significantly.

The method of the present invention is thus to be distinguished from prior art, such as U.S. Pat. No. 6,173,604, which utilizes a scanning microwave microscope having a sharpened conducting tip extending through the end wall of a resonator, to reduce the effect of the propagating wave. Such a known probe, cannot be used to measure biological tissue without harming the tissue itself; furthermore, the evanescent wave of such a known probe will penetrate into the whole human body. Also, since such a known technique relies on average power measurement, and not on voltage measurement, it is not able to calculate dielectric properties in the time domain. Also, the frequency range in such method is in the microwave region of the electromagnetic spectrum. Further differences are that it is not flexible and cannot be hand-held.

Still further features and advantages of the invention will be apparent from the description below.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

PRIOR ART PROBE CONSTRUCTIONS

Figure 1A:
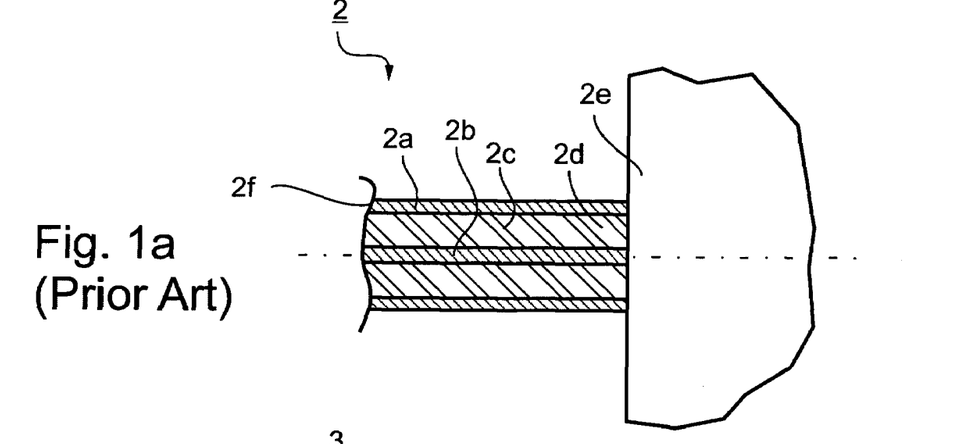
FIGS. 1a–c illustrate three prior art probes for examining tissue in order to differentiate it from other tissue according to the dielectric properties of the examined tissue.
Figure 1B:
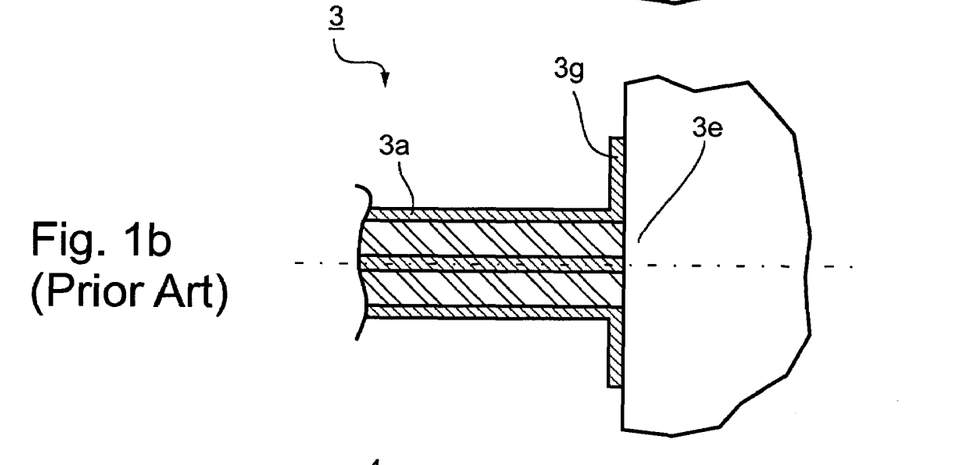
Figure 1C:
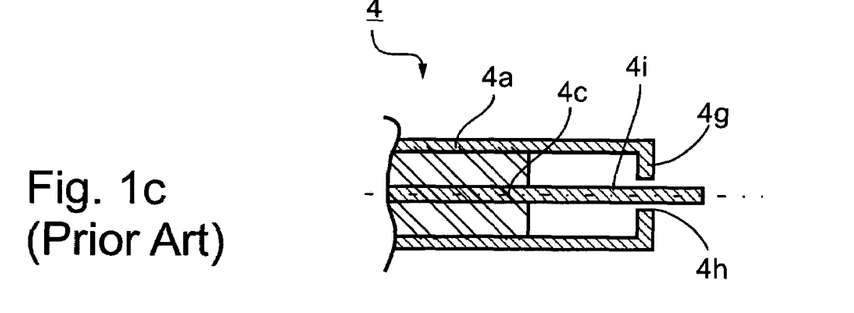

FIGS. 1a–1c illustrate typical prior art constructions of probes for examining tissue as briefly discussed above.

Thus, FIG. 1a illustrates a prior art probe 2 including an outer electrical conductor 2a and an inner electrical conductor 2b insulated from the outer conductor by a dielectric 2c. When an electrical pulse is applied to end 2f of the probe 2, the tissue 2e closing the open cavity 2d of the probe will generate a reflected pulse. The generation of such a reflected pulse, however, will involve both near field and far field radiation because the ends of the two conductors 2a, 2b terminate in the same plane. The reflection mechanism is strongly dependent on the reflection of the far field, so that the dielectric parameters of the generated reflected pulse are actually averaged over the relatively large body of tissue 2e, with no enhancement of the electric field near the sampled tissue.

FIG. 1b illustrates a probe 3 of a similar construction, except that the outer conductor 3a is provided with an outturned flange 3g engaged by the examined tissue 3e. The reflection mechanism in probe 3 illustrated in FIG. 1b will therefore be similar to that described above with respect to probe 2 in FIG. 1a.

FIG. 1c illustrates a probe 4 similar to that described in FIG. 1a, except that the outer conductor 4a is formed with an end wall 4g having a small opening 4h therein, and the inner conductor 4c is formed with a sharpened tip 4i extending through opening 4h in the end wall of the outer conductor. Such a construction produces a resonator which does reduce the propagating wave. However, this probe construction cannot be effectively used to measure biological tissue without harming the tissue. In addition, the evanescent wave produced by that probe will penetrate into the whole human body. Further, such a probe relies on average power measurement, and not on voltage measurement, and therefore it is incapable of calculating dielectric properties in the time domain. Moreover, such a probe generally operates in the microwave region of the electromagnetic spectrum. Finally, such probes are generally not flexible and cannot be hand-held.

PREFERRED EMBODIMENTS OF THE PRESENT INVENTION

Figure 2:
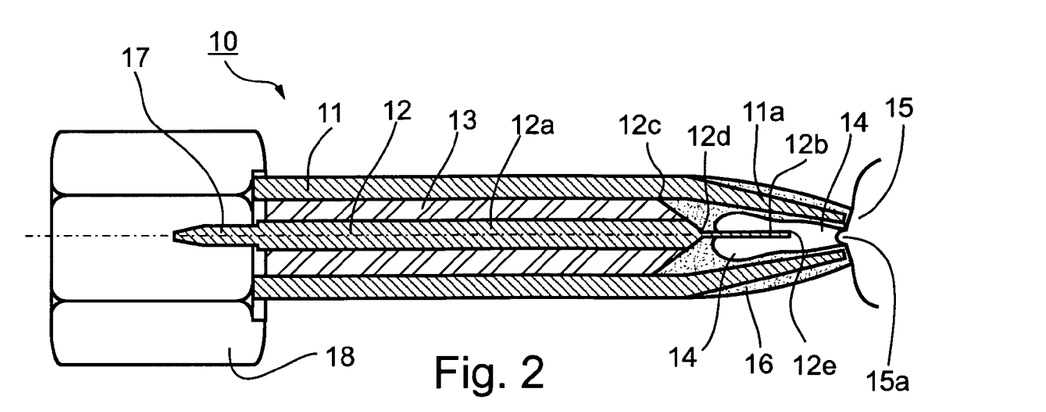
FIG. 2 schematically illustrates one form of probe constructed in accordance with the present invention for examining tissue in order to differentiate it from other tissue according to the dielectric properties of the examined tissue.

FIG. 2 illustrates a probe constructed in accordance with the present invention and, which provides one or more advantages, in the above respects with respect, to the prior art constructions illustrated in FIGS. 1a–1c.

The probe illustrated in FIG. 2, and therein generally designated 10, also includes an outer conductor 11 and an inner conductor 12 insulated from the outer conductor by a body of insulation 13. For example, the outer conductor 11 may be of aluminum, the inner conductor 12 of copper, and the dielectric 13 of a fluorinated polymer, such as "Teflon"™. The inner and outer conductors are open at one end to define an open cavity 14 which is applied to, and closed by, the tissue 15 being examined. In this case, however, the open end of the outer conductor 11 extends slightly past the inner conductor 12 in the axial direction, such that the inner conductor 12 terminates inwardly of the outer conductor within the open cavity 14.

Preferably, the end of the insulation body 13 defining the open cavity 14 is covered by a thin, soft layer of insulation 16, such as a silicone film, e.g., applied by dipping or spraying.

The probe illustrated in FIG. 2 is used in the same manner as described above with respect to FIG. 1a, in that the open cavity 14 of the probe is applied against the tissue 15 being examined such that the tissue closes the open cavity. However, since the tissue 15 is deformable by the end of the probe, and since the inner conductor 12 terminates inwardly of the outer conductor 11, a portion of the tissue is caused to penetrate within the open cavity, as shown at 15a.

Other differences in the probe illustrated in FIG. 2, over the prior art construction illustrated in FIG. 1a, are that the outer conductor 11 is tapered at the outer end 11a, and the tip of the inner conductor 12 within the open cavity 14 is reduced in diameter to form a large-diameter section 12a, a small-diameter section 12b, relatively sharp annular edges 12c and 12d at the juncture of these two sections, and a sharp annular edge 12e at the outer tip of section 12b, all within the open cavity 14.

At the opposite end, the probe is connected to an SMA type jack 17, and to an SMA type connector 18.

As one example, the length of the probe may be 10 mm and have an outer diameter of 3.5 mm; the inner conductor 12 may be of a length of 9 mm and of a diameter of 1.0 mm, whereas its tip may be of a length of 1 mm and a diameter of 0.1 mm; and the thin insulation layer 16 may be of silicone rubber or of a varnish and have a thickness of approximately 30 μm.

Such a probe construction provides a number of advantages. Thus, the generation of the reflected pulse produced in the open cavity 14 is accompanied by negligible radiation penetrating into the body connected to the examined tissue 15. In addition, the provision of the two diameters in the inner conductor 12, particularly the sharp annular edges 12c, 12d and 12e of the two conductor sections 12a, 12b within the open cavity 14, produces a concentrated electrical charge at these edges which enhances the electrical field between the inner conductor and the outer conductor precisely in the region receiving the examined tissue 15. Therefore, most of the energy dissipation in the probe illustrated in FIG. 2 takes place within the small portion 15a of the examined tissue penetrating into the open cavity 14 of the probe; the remaining energy is reflected back to the transmission line connected to the opposite end of the probe. In addition, the enhancement of the electrical field in the tissue zone leaves almost no energy outside that zone to penetrate into the body of the tissue.

Figure 3A:
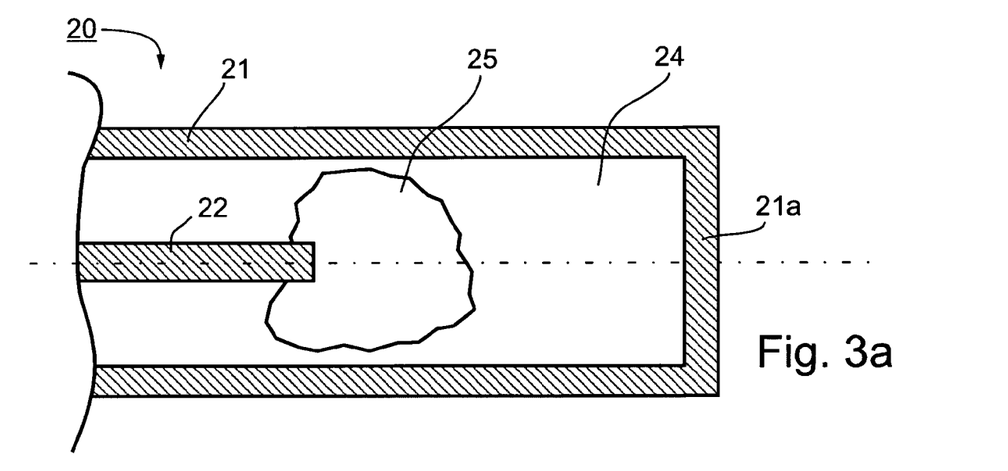
FIGS. 3a–3b are diagrams helpful in explaining the present invention.
Figure 3B:
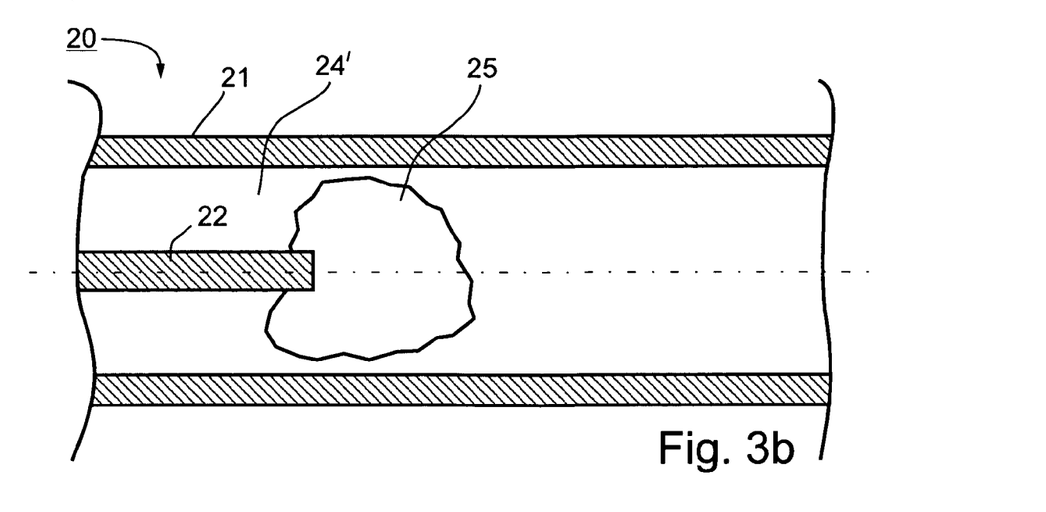

Although the exact theoretical calculation is quite difficult, the physical mechanism of the operation of the probe illustrated in FIG. 2 can be illustrated by the two cases diagrammatically illustrated in FIGS. 3a and 3b.

FIG. 3a illustrates a theoretically ideal case for examining tissue, wherein the a probe 20 includes a closed cavity 24 defined by an outer conductor 21 having an end wall 21a, and an inner conductor 22. An examined tissue 25 is placed completely within the closed cavity 24. Since the tip of the inner conductor 22 is surrounded by the tissue 25, it is clear that no radiation leakage can occur outside of the cavity which is fully closed by the outer conductor 21. The reflected pulse will therefore be influenced by the impedance of the examined tissue 25. Such a construction might be practical in off-line testing of biological tissue, but not in applications requiring on-line or real-time testing of tissue where the tissue to be examined is still connected to the main tissue body.

FIG. 3b illustrates a case wherein the examined tissue 25 is completely within an open cavity 24' defined by the outer conductor 21 and the inner conductor 22, but here the outer conductor extends for a considerable distance past the inner conductor so as to fully enclose the tissue being examined. In such a construction, the radiation leak is again negligible, but the construction is not practical for real-time examination of tissue since the length of the open cavity is too long for the examined (living) tissue to penetrate into it as shown without separating it from the main tissue body.

Figure 4:
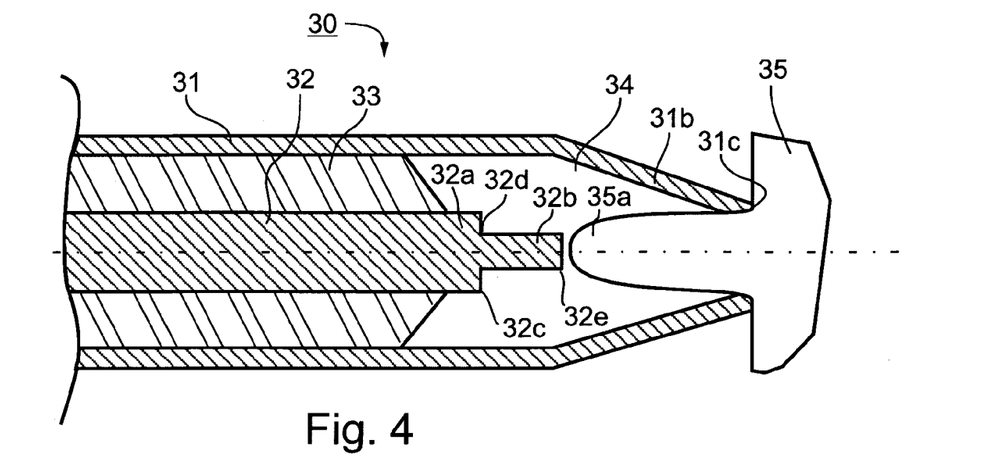
FIG. 4 diagrammatically illustrates a probe constructed in accordance with one embodiment of the invention.

FIG. 4 illustrates a probe construction according to the present invention and similar to that of FIG. 2. Thus, probe 30 also includes an outer conductor 31 and an inner conductor 32 insulated therefrom by insultation 33 and terminating slightly inwardly of the outer conductor so as to define an open cavity 34 to be penetrated by the body of the tissue 35 being examined. Also in the probe illustrated in FIG. 3, as in FIG. 2, the tip of the inner conductor 32 within the open cavity 34 is reduced in diameter to define a large-diameter section 32a, being a general diameter section, a small-diameter section 32b, and sharp annular edges 32c, 32d and 32e, enhancing the electrical field within the cavity 34.

In probe 30 illustrated in FIG. 4, the tissue end of the outer conductor 31, which defines the open cavity 34, is reduced in diameter to define a tapered section 31b and a relatively small diameter opening 31c for receiving the body of tissue 35 being examined. However, the deformability of tissue 35 permits a significant portion thereof, shown at 35a, to enter the cavity 34, and thus to influence the reflected pulse generated therein.

Figure 5:
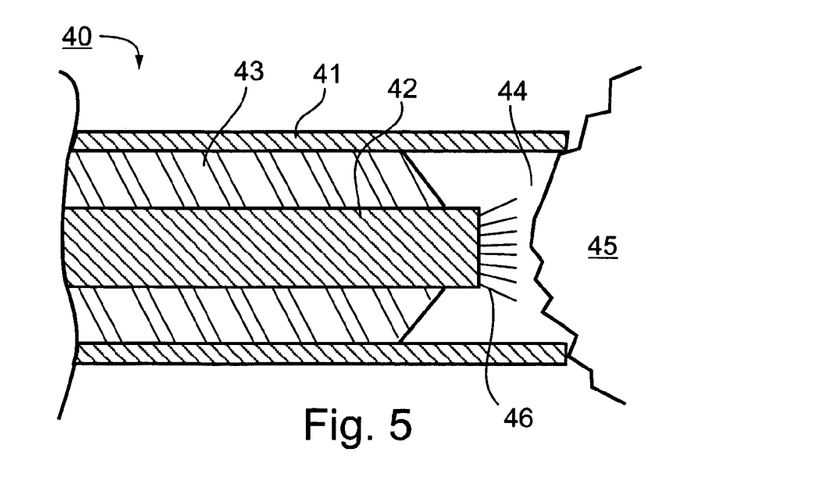
FIG. 5 diagrammatically illustrates a probe constructed in accordance with another embodiment of the invention.

FIG. 5 illustrates another probe 40 constructed according to the present invention in that it also includes an outer conductor 41 and an inner conductor 42 insulated therefrom by insulation 43, with the inner conductor terminating inwardly of the outer conductor to define an open cavity 44 for receiving the tissue 45 to be examined, similar to the construction of FIG. 2. In this case, however, the electrical fringe field within the cavity 44 is enhanced by providing the tip of the inner conductor 42, located within the open cavity 44, with a plurality of sharps thin, projections or spikes 46. Preferably, projections or spikes 46 are from a few microns to a few tens of microns in diameter, and are of an electrically-conductive material such as stainless, copper, aluminum, graphite nanotubes, etc.

Figure 6:
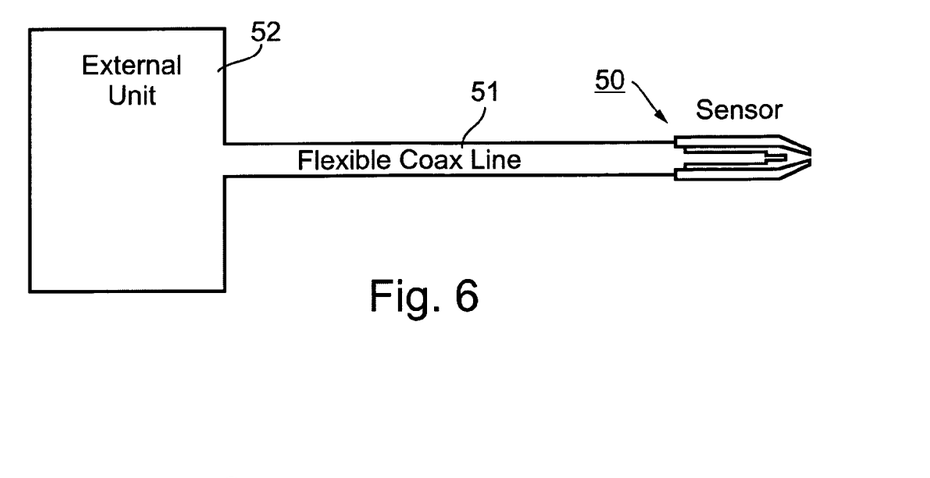
FIG. 6 diagrammatically illustrates a probe constructed in accordance with the invention connected to an external unit by a flexible coaxial line.

FIG. 6 illustrates an assembly including a probe 50, such as that illustrated in FIG. 4, coupled to one end of a flexible coaxial line 51; the opposite end of coaxial line 51 is connected to an external unit 52 for supplying the pulses to the probe. The external unit 52 is more particularly illustrated in FIG. 7, as including a computer 53, a pulse source 54 and a digitizing unit 55.

When connected to the probe 50, the line 51 is as close as possible to an ideal open line. In general, the electric field mode over the aperture defined by the open cavity (e.g. 34, FIG. 4) at the probe (30, FIG. 4), and closed by the examined tissue (15) in the coaxial mode is given by the following equation:

$$Er = -V/[r\log(b/a)] \qquad \text{(Eq. 1)}$$

where: "V" is the voltage between the central and outer conductors is the inner conductor radius; and "b" is the outer conductor radius. When the inner conductor is formed with the sharp annular edges in the open cavity (e.g., edges 12c–12e, FIG. 2, or edges 32c–32e, FIG. 4), to enhance the electrical field within the open cavity, the radius "a" should be appropriately modified.

When the inner conductor ends before the end of the line as shown, the electric field in the open-cavity zone formed at the end of the line is the fringing field of the coaxial mode; in that case there is no far field radiation and almost no near-field outside the coaxial line.

Also, when the tip of the inner conductor is reduced in diameter as shown in FIG. 2 or FIG. 4, and particularly when it is connected to much thinner elements such as the plurality of projections or spikes as shown in FIG. 5, the electric field mode around those elements is changed from the coaxial mode to a modified coaxial mode, producing a much stronger electrical fringing field near the elements. The deformation of the biological tissue allows it to penetrate into the space of the open cavity at the end of the probe between the center conductor and the outer conductor. In this way, a small portion of the biological tissue is placed in the electric fringing field and is responsible for most of the reflection of the applied voltage pulse back into the transmission line 51. Most of the reflection thus occurs inside the probe itself; also both the evanescent waves and the propagating waves are substantially eliminated. The output impedance of the probe thus depends to a great extent on the impedance of the biological tissue. As a result, the reflected pulse detected by the probe is dependent substantially on the dielectric properties of the tissue itself, and not, as in the case where the tissue is sampled by a conventional open-ended coaxial line, on the dielectric properties of the surroundings. This allows the sampled tissue impedance to be calculated without affecting, or being affected by, the surrounding tissues.

Figure 7:
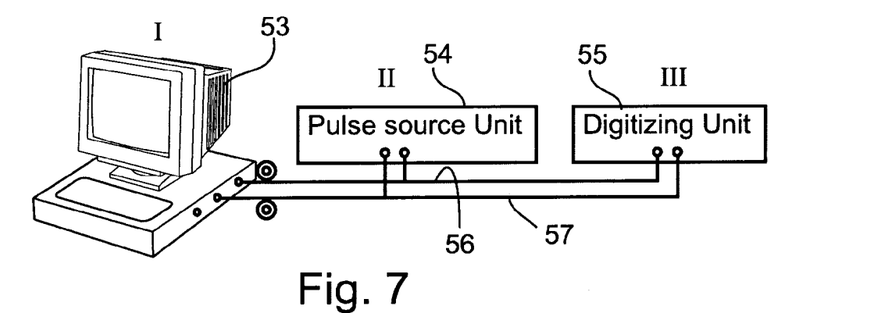
FIG. 7 diagrammatically illustrates the components of the external unit in the system of FIG. 6.

As shown in FIG. 7, two sets of wires 56, 57 connect the computer 53 to the pulse source unit 54 and the digitizing unit 55. One set of wires 56 are the timing control wires used to transmit trigger signals to the pulse source unit 54 and the digitizing unit 55; whereas the other set of wires 57 are the data transfer wires used to transfer data from and to the computer 53.

The computer 53 controls the pulse durations and repetition rates, as well as the pulse voltage. Preferably, the pulses should have a duration of the order of nanoseconds or picoseconds. The repetition rates may be of a few Herz to a few giga-Herz.

Figure 8:
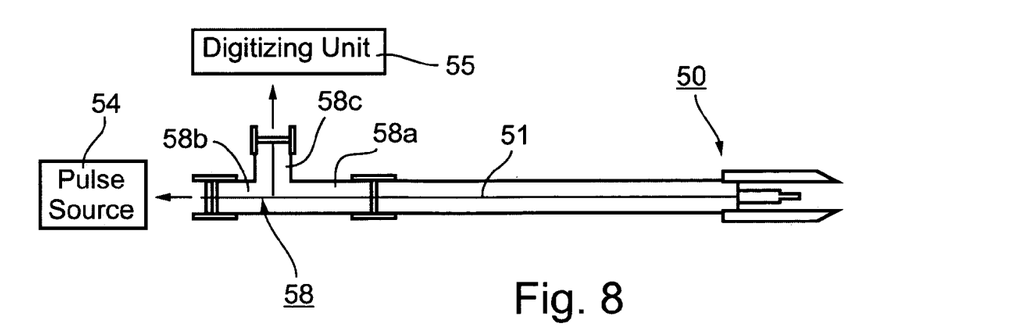
FIG. 8 illustrates the connector between the external unit components and the coaxial line to the probe in FIGS. 4 and 5.

FIG. 8 illustrates the electrical connections between the flexible coaxial line 51 connected at one end to the pulse source unit 54 and the digitizing unit 55, and at the opposite end to the probe 50. As shown in FIG. 8, these connections are made by a T-connector 58 having one leg 58a connected to the coaxial line 51, a second leg 58b connected to the pulse source unit 54, and a third leg 58c connected to the digitizing unit 55.

The pulses generated in the pulse source unit 54 are split by connector 58 into two signals. One signal goes to the digitizing unit 55, and the other to probe 50 via the coaxial line 51. The voltage pulses (e.g., 4–10 volts) reach the probe 50 and are reflected back from its tip according to the dielectric properties of the examined tissue closing the open cavity (e.g., 34, FIG. 4) at the end of the probe (30, FIG. 4). The reflected pulses are also split by the T-connector 58, a part being directed to the pulse source 54, and another part to the digitizing unit 55. The part of the reflected pulse received by the pulse source 54 could be absorbed by a resistor, or reflected back, if desired to provide multiple reflections in order to enhance the tissue effect on the signal as more particularly described below.

Figure 9A:
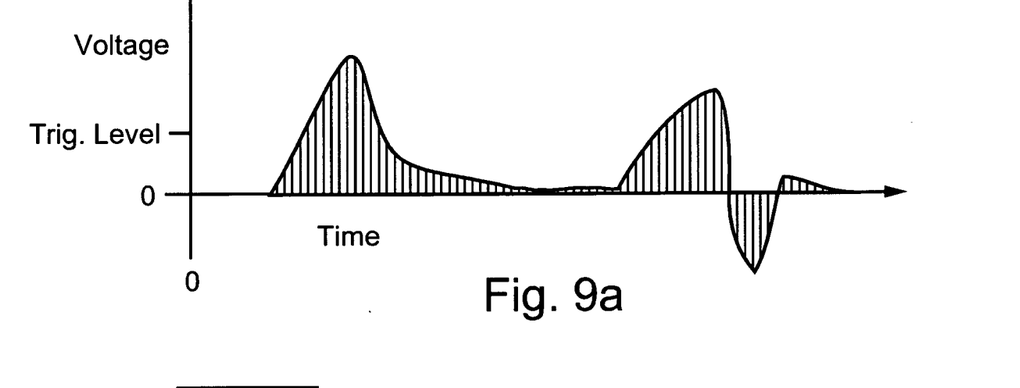
FIGS. 9a–9b illustrate the digitizing process of both the incident and reflected signals, and the resulting data array.
Figure 9B:
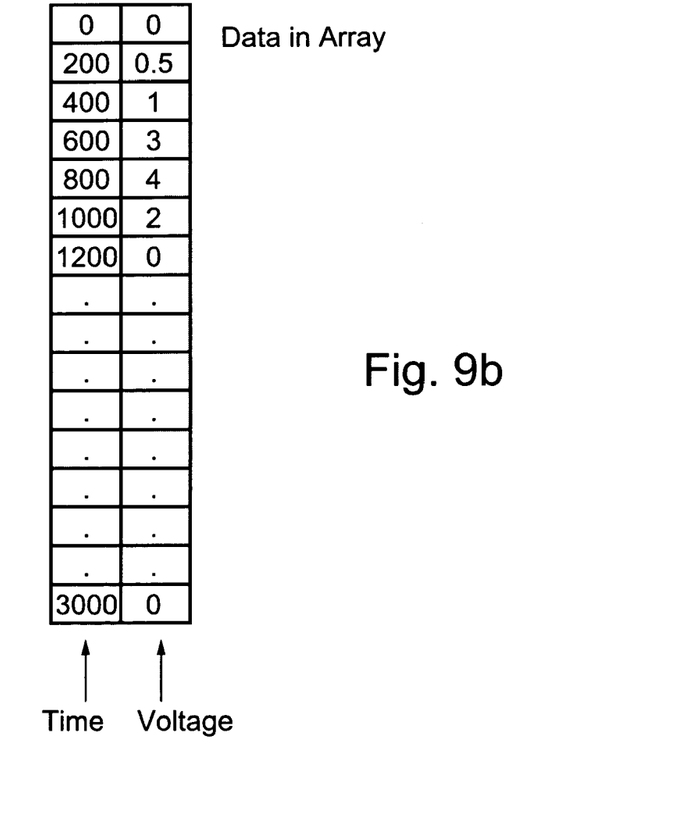

Digitizing unit 55 samples, at a plurality of spaced time intervals, both the incident electrical pulse, namely that applied to the probe 50, and the reflected pulse reflected by the examined tissue closing the cavity at the end of the probe. FIG. 9a illustrates the sampling process, wherein it will be seen that samples of the voltage levels are taken of the two pulses over a plurality of spaced time intervals. For example, the sampling rate may be 5 GHz, providing 200 picosecond samples. FIG. 9b illustrates a typical data array produced as a result of this sampling operation.

Each data array contains two voltage pulses, i.e., incident and reflected. The computer program divides the data array into two equal arrays, each array now corresponding to one pulse.

Figure 10A:
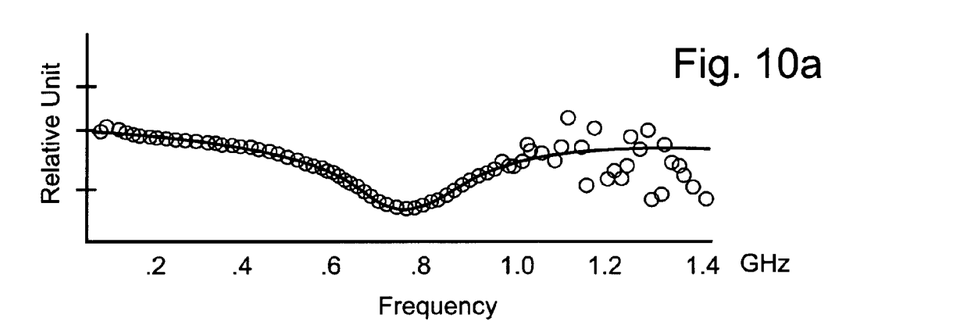
FIGS. 10a–10d are graphs illustrating the manner of comparing the, electrical characteristics of reflected pulse produced by the examined tissue with the incident pulse applied to the examined tissue.
Figure 10B:
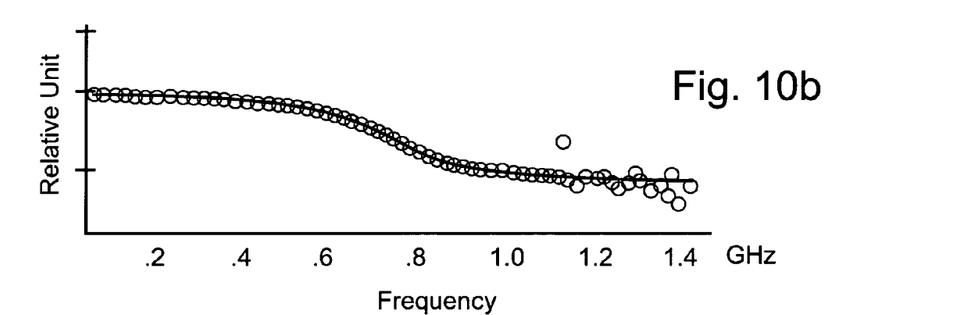
Figure 10C:
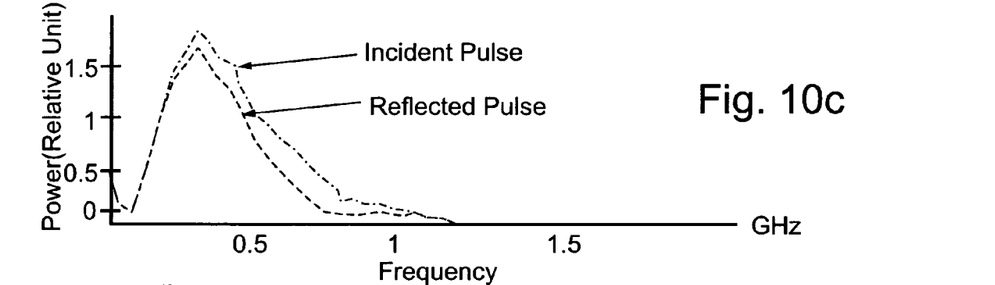
Figure 10D:
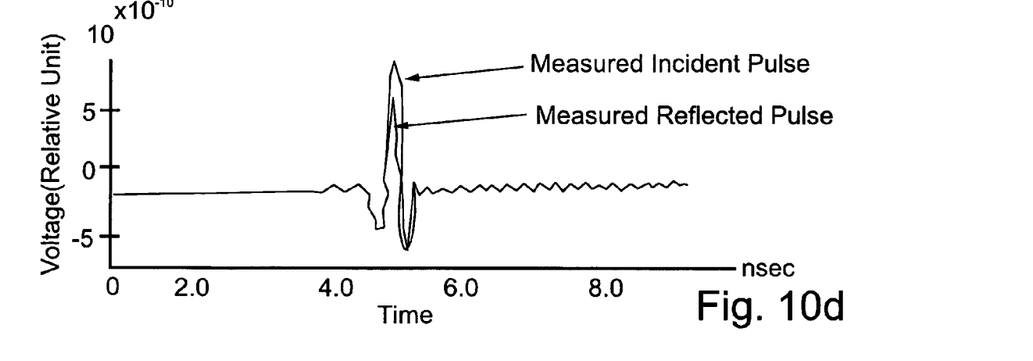

The two time-domain arrays are now transformed to the frequency domain by a conventional FFT program, which is a standard tool for transforming time domain signals to the frequency domain. FIG. 10a illustrates the phase graph (phase, frequency) of the reflected pulse, whereas FIG. 10b illustrates the same graph for the incident pulse. FIG. 10c illustrates an example of the two pulses at the real-amplitude frequency graph; and FIG. 10*d* illustrates actual measurements of the incident pulse and the reflected pulse.

The above-described procedure is repeated, e.g., 1,000–10,000 times, for each measurement point. This result is 1,000–10,000 pairs of arrays, all of which are saved and transmitted to the analysis program of the computer 53.

Computer 53 compares the electrical characteristics of the reflected electrical pulse with respect to those of the incident (applied) electrical pulse to provide an indication of the dielectric properties of the examined tissue. This is done by sampling both electrical pulses at a plurality of spaced time intervals, and comparing the voltage magnitudes of the two electrical pulses at the spaced time intervals.

The foregoing comparison is made in a three-level analysis according to: (1) a dielectric function calculation, (2) a Cole-Cole parameters calculation, and (3) three-dimensional similarities.

In the dielectric function calculation analysis, the theoretical value of the reflection coefficient $\Gamma$ can be given by the following equation:

$$\Gamma = [Z_1 - Z_0]/[Z_1 + Z_0] \quad \text{(Eq. 2)}$$

where: $Z_1$ is the impedance of the probe plus the impedance of the examined tissue; and $Z_0$ is the impedance of the transmission line.

Since $Z_1$ is a dielectric function of the examined tissue, the dielectric function can be calculated from the function $Z_1$. In a normal incident pulse, $Z = \in^{1/2}$. So when $\Gamma$ is known, $\in(\omega)$ of the tissue can be calculated by the equation:

$$\in(\omega) = Z_0(\Gamma + 1(1 - \Gamma) \quad \text{(Eq. 3)}$$

where: $\Gamma$ is the theoretical reflection coefficient; $Z_0$ is the cable and empty probe impedance; $Z_1$ is the tissue impedance; and $\in(\omega)$ is the tissue dielectric function.

The experimental reflection coefficient $R(\omega)$ is calculated from the following relation of the measured signals at the frequency domain:

$$R(\omega) = E(\omega)\text{reflected}/E(\omega)\text{incident} \quad \text{(Eq. 4)}$$

where: $E(\omega)$reflected is the reflected signal array; and $E(\omega)$ incident is the incident signal array at the respective frequency ($\omega$).

After the dielectric function of the examined tissue is calculated, it is analyzed according to the following considerations:

The computer calculated the values of extreme point (Peaks) and special features, like the frequency at which the extreme points appear, the amplitude of the peaks, the average value of the function, the integral under the real part of the dielectric function, the average value of the derivative, the maximum derivative, and the roots of the function. All these values are transferred as an array to the decision-making program routine. For each value the statistical variance is also calculated.

When the impedance of the source is much larger than the impedance of the cable, typically 50 ohms, the reflected pulse will be reflected again and will reach the probe. The multiply reflection can be described by $\Gamma^n$, where "n" is the number of the reflections. Providing such multiple-reflections produces enormous enhancements of the examined tissue parameters since the effect of the bio-tissue impedance is now multiplied. In the multiple-reflection mode, the $5^{th}$ reflection is preferably used to characterize the tissue. The logic of the calculations is the same as in the case of first reflection.

In the Cole-Cole Parameter analysis the Cole-Cole parameters $\tau$ and $\alpha$ of the sampled tissue are calculated from the dielectric function as follows:

$$\varepsilon = \varepsilon_\infty + \frac{\Delta\varepsilon}{1 + (j\omega\tau_c)^{1-\alpha}}, \Delta\varepsilon = \varepsilon_s - \varepsilon_\infty \quad \text{(Eq. 5)}$$

Where: e is the dielectric function of the sample; $\in_\infty$ is the dielectric function at infinite frequency=constant; $\in_0$ is the dielectric function under dc field=constant; and j is $(-1)^{1/2}$ For each value, the statistical variance is also calculated. After calculation, the Cole-Cole parameters are transferred to the decision-making program routine.

In the 3D similarities analysis the dielectric function is drawn as a 3D curve in the 3D phase space constituted of the real-part dielectric function, the imaginary-part dielectric function, and the frequency. The 3D curves are analyzed with respect to total volume, extreme points, curvature, and cross-section as a function of frequency and overlapping, and are computed with previously stored values of known normal and cancerous tissues. The 3D volumes are displayed at the user interface together with pre-measured known-tissue volumes.

The decision making routine compares the results from the three levels of analysis and the existing data from the memory bank. In the memory bank, data from known types of tissue is recorded, together with the tissue type name and the statistical variance. The statistical variance is used to define a volume surrounding the curve.

The matching condition is a standard statistical process which compares two sets of data. It uses all data for comparison. For example, if the data matches data from a previously taken memory bank data, the program displays the type of tissue from which the databank sample was taken.

In case there is no match between stored (known) tissue data and the examined tissue data, the most similar stored tissue data is chosen as characterizing the examined tissue. The most similar tissue is chosen according to the distance (in the phase space) between the two measured points; alternatively, a user defined criterion may be applied. The user may decide to find similarities, at certain measurement points, based on one, two, or more specific calculated parameters, ignoring all the others. For example the user may decide to find similarities only according to the frequency at which a peak appears in the real-part of the dielectric function.

The decision making routine also compares the last-point measured to the currently measured point. The result of that process is to indicate merely how similar the two points are to each other, without knowing the type of tissue of the last point. The distance between two data points is considered as usually in statistics, and the decisions are displayed on the screen together with all data parameters.

Figure 11:
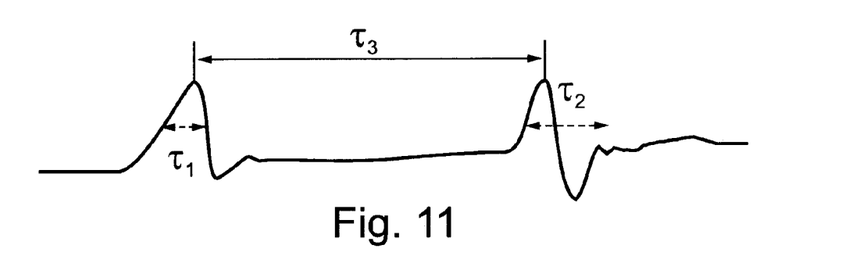
FIG. 11 illustrates a typical incident pulse and a typical reflected pulse whose electrical characteristics are compared.

FIG. 11 shows a pair of pulses as measured by the digitizing unit. The first one is the incident (applied) pulse, and the second one is the reflected pulse. $\tau 1$ is the duration of the first pulse; $\tau 2$ is the duration of the reflected pulse; and $\tau 3$ is the time interval between the pulses. The time interval is the transit time for the pulse to reach the probe and back. This time is equal to 2 LE/c, where "L" is the length of the cable, "E" is the dielectric constant of the cable insulator, and "c" is the light velocity. The data acquisition time of this pair is about 10 nsec. In that time interval, any mechanical movement is insignificant; accordingly, any movement of the operator's hand, or of the body containing the tissue to be examined, will not affect the measurement.

Figure 12:
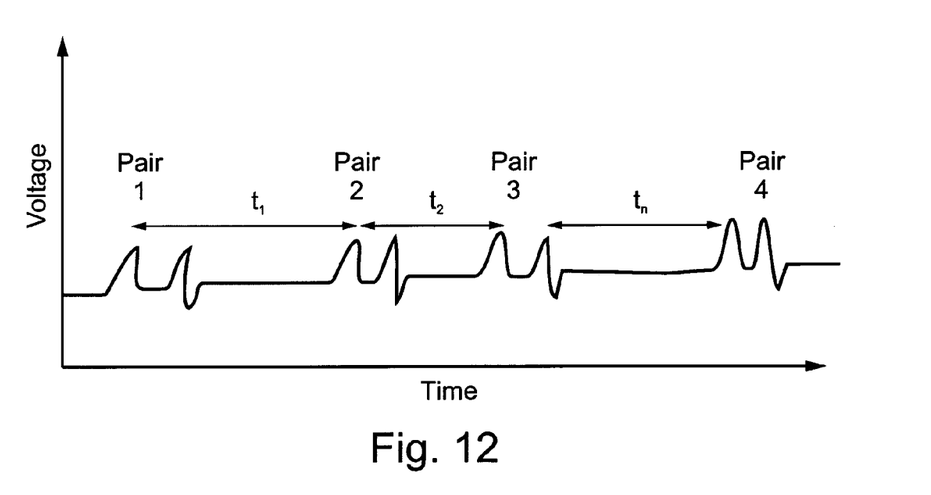
FIG. 12 are waveforms helpful in explaining the manner in which the electrical characteristic of the incident and reflected electrical pulses are compared.

FIG. 12 illustrates a plurality of pairs of such pulses wherein $t_i$ (of $t_1-t_n$) is the time at which the peak of the incident pulse appears in the digitizing unit. Therefore, $t_i$ is the time between pairs. Generally, $t_i$ is different fron $t_{i+j}$ ("i" and "j" are index numbers) since there is relative movement between the probe and the tissue.

By repeating this procedure according to the present invention, many pair of pulses are collected and the amplitude and phase of each pair is calculated separately, which thereby eliminates the phase noise existing in the usual way of measurements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

REFERENCES

1. D. J. Winchester and D. P. Winchester. Atlas of Clinical Oncology Breast Cancer. B. C. Decker, Inc. 2000.
2. M. A. Stuchly, et al., "Measurement of Radio Frequency Permitivity of Biological Tissues With an Open-Ended Coaxial Line: Part I and II," IEEE Trans, Microwave Theory Tech., Vol. MTT-30, pp. 82–92, April 1980.
3. D. Misra, et al., "Non-Invasive Electrical Characterization of Materials at Microwave Frequencies Using Open Ended Coaxial Line: Test of an improved calibration technique." IEEE Trans. Microwave theory tech. Volume MTT-38, pp. 8–13, January 1990.
4. E. C. Burdette, et al., "In Vivo Probe Measurement Technique for Determining Properties at VHF Trough Microwave Frequencies," IEEE Trans. Microwave Theory Tech. Vol. MTT-28, pp. 414–427, January 1980.
5. Surowiex, A. J. et al., 1988, Dielectric Properties of Breast Carcinoma and the Surrounding Tissues, IEEE Trans. Biomed. Eng. 35(4):257–262.
6. Heintz, J. & O. Minet, 1995 Dielectric Properties of Female Breast Tumors, In Ninth International Conference on Electrical Bio-Impedance, Heidelberg.
7 Lies, D. et al., 1998 Clinical Study on Electrical Impedance Method Used Diagnosis of Breast Diasi. In Tenth International Conference on Electrical Bio-Impedance. Barcelona.
8. Morimoto, et al., Measurement of Electrical Bio-Impedance of Breast Tumors, Eu. Serg. Res. 2292:86–92, 1990.
9. S. Grimnes & O. G. Martinsen. "Bioimpedance and Bioelectricity Basic. Academic Press 2000.
10. Kinouch, Y et al., Fast In-Vivo Measurement of Local Tissue Impedance Using Needle Electrodes, Med. Biol Eng. Comput. 35(9):486–492, 1997.
11. Yuken Ohmine, et al., Non-Invasive Measurement of the Electrical Bio-Impedance of Breast Tumors, Anti Cancer Research 20:1941–1946 (2000).
12. Lever-Moskovitz, O. 1996. T-Scan: A New Imaging Method for Breast Cancer Detection Without X-Ray. RSNA., '96, Chicago.
13. Dexter, G. et al, "In-Vivo Measurement of Tumor Conductiveness With Magnetic Bioimpedance Method", IEEE Trans Biomedical Engine", Vol. 47 No. 10 October 2000.
14. Prthig, R., (1978), Dielectric and Electronic Properties of Biological Materials, John Wiley, New York.
15. Schanna, O. F. et al., (1978), Impedance Measurement in Biological Cell. John Wiley, New York.
16. H. P. Schwan, Mechanisms Responsible for Electrical Properties of Tissue and Cell Suspensions, Med. Prog. Tech. 19:163–165, 1993.
17. Fricke, H. The Theory of Electrolytic Polarization. Philosophical Magazine 1932; (97):310–318.
18. Cole K S (1972) Membranes, Ions (1978) and Impulses. University of California Press, Berkeley.
19. Cole, K. S &. Cole. R. H 1941, Dispersion and Absorption in Dielectrics. J. Chem. Phys. 9:341–351.
20. Juan R. Mosig, et al., Reflection of An Open-Ended Coaxial Line and Application to Nondestructive Measurement of Materials. IEEE Trans. Inst. Measr. Vol. IM-30, No. 1, March 1981.
21. U.S. Pat. No. 6,173,604.
22. Xu, Y., et al. "Theoretical and Experimental Study of Measurement of Microwave Permitivity Using Open Ended Elliptical Coaxial Probes". IEEE Trans AP-40(1), January 1992, pp 143–150.3.
23. Proakis, John G., Digital Signal Processing, Chapter 4, Prentice-Hall International Inc.

What is claimed is:

1. A probe for tissue examination by dielectric properties, the probe comprising:
   an inner conductor, which defines a general diameter section and a proximal end with respect to a tissue for examination;
   an insulation layer, which substantially surrounds the inner conductor; and
   an outer conductor, which substantially surrounds the inner conductor and the insulation layer,
   the probe being configured for applying an electric pulse to the tissue for examination, generating electrical fringe fields in the tissue, in a near field, responsive to the electric pulse, applied thereto, thus producing a reflected electric pulse from the tissue for examination,
   wherein the inner conductor includes at least one section of a different cross-section from that of the general diameter section, the different cross section leading to sharp edges,
   wherein concentrated electrical charges at the sharp edges enhance the electrical fringe fields at the proximal end, where interaction with the tissue for examination occurs,
   and wherein the at least one section of the different cross-section comprises a plurality of sharp, thin, conductive spikes, which enhance the electrical fringe fields at the proximal end, where the interaction with the tissue for examination occurs.

2. The probe of claim 1, wherein the conductive spikes range in cross section from about 2 microns to about 200 microns.

3. The probe of claim 1, wherein the outer conductor extends beyond the inner conductor, at the proximal end, to define an open cavity.

4. The probe of claim 3, wherein the outer conductor comprises a tapered section at the proximal end, reducing the opening of the open cavity.

5. The probe of claim 3, wherein the open cavity is adapted to be enclosed by the tissue for examination, such that the tissue for examination experiences the electrical fringe fields within the open cavity.

* * * * *